United States Patent [19]

Mraz

[11] Patent Number: 5,018,389
[45] Date of Patent: May 28, 1991

[54] ROCK-STRESS MEASURING METHOD
[75] Inventor: Dennis Mraz, Saskatoon, Canada
[73] Assignee: Engineered Instruments, Inc., Saskatoon, Canada
[21] Appl. No.: 462,595
[22] Filed: Jan. 9, 1990
[51] Int. Cl.⁵ .......................................... G01N 33/24
[52] U.S. Cl. .................................................. 73/784
[58] Field of Search ............... 73/784, 768; 116/212, 116/DIG. 34

[56] References Cited
U.S. PATENT DOCUMENTS

| 4,542,655 | 9/1985 | Park et al. | 73/784 |
| 4,543,820 | 10/1985 | Handy et al. | 73/784 X |

FOREIGN PATENT DOCUMENTS

| 568701 | 8/1977 | U.S.S.R. | 73/784 |
| 631585 | 11/1978 | U.S.S.R. | 73/784 |

Primary Examiner—Jerry W. Myracle
Attorney, Agent, or Firm—Staas & Halsey

[57] ABSTRACT

A method and apparatus of measuring rock-stress uses a tapered sensing plug which is wedged into a conically shaped end portion of a borehole. A rod is used to place the sensing plug in position, to orient the plug relative to its longitudinal axis for sensing stress in a particular direction, and to prestress the sensing plug by causing same to be wedged in the tapered portion of the bore.

4 Claims, 1 Drawing Sheet

ROCK-STRESS MEASURING METHOD

BACKGROUND OF THE INVENTION

1. Field of the Invention

The present invention relates generally to an apparatus and method for measuring stresses in a rock mass, and more specifically, to a method and apparatus employing a strain gauge in a borehole.

2. Description of the Related Art

Stress measurement in rock is carried out extensively in fields such as mining, civil engineering (highways, bridges, dams), and geology. Accurate and appropriate stress data are extremely important because they often play a significant role in the stability of the rock mass or structure being monitored.

Rock stress measurement is commonly performed by drilling a borehole in the rock and installing one or more sensors composed of photoelastic plugs, flat jacks, vibrating wire gauges, or load cells. The signals from these sensors are read by equipment designed to process the data into values indicative of the rock stress, by application of calibration factors or analytically developed equations.

Commercially available borehole stress-meters are deficient in that they are expensive, complicated, and difficult to install and use. For example, conventional meters require highly skilled technicians and/or engineers for proper placement of the sensors and the installation process is very time consuming. Also, conventional stress meters often need to be "bonded" in place for proper operation and are seldom removable for reuse.

A borehole stress-meter and method and apparatus for the installation thereof is described in U.S. Pat. No. 4,542,655. The apparatus and method requires a resiliently radially expandable hollow body within which can be positioned a gauge plug having strain gauges fixed thereto. The interior section of the hollow body is tapered, as is the gauge plug so that advancement of the gauge plug within the hollow body will cause the gauge plug to become prestressed. The hollow body can be inserted into a cylindrical bore drilled in earth material, whose stress is to be measured, by an installation or setting tool. Subsequentially, the gauge plug is advanced within the hollow body so as to prestress the gauge plug. The setting tool is then removed and stress may be measured by an appropriate strain indicator.

SUMMARY OF THE INVENTION

An object of the present invention is to provide a rock-stress measuring device which is inexpensive to produce, mechanically simple, and easy to operate.

These and other objects of the invention are met by providing a method of measuring rock stress which includes drilling a cylindrical borehole into earth material at a length short of a desired depth of placement, drilling beyond the first length with a tapered bit to form a conically shaped inward end portion of the cylindrical borehole, inserting a tapered sensing plug preferably with the same conicity as the tapered bit into the conically shaped inward end portion of the cylindrical borehole, setting the sensing plug at a predetermined orientation firmly in the conically shaped inward end portion of the cylindrical borehole, and processing signals output by the sensing plug to determine rock-stress data.

In another aspect of the present invention, an apparatus for measuring rock-stress includes a sensing plug having two opposing tapered sidewalls, and means coupled to the sensing plug for processing signals output from the sensing plug to determine rock-stress data.

These and other features and advantages of the method and apparatus for measuring rock-stress according to the present invention will become more apparent with reference to the following detailed description and drawings.

DETAILED DESCRIPTION OF THE PREFERRED EMBODIMENTS

Figure 1:
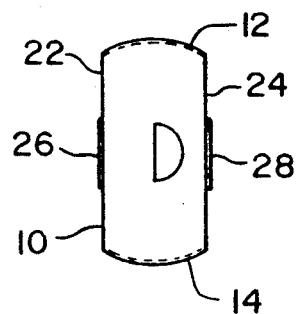
FIG. 1 is an end view of a first, preferred embodiment of a sensing plug according to the present invention.
Figure 1A:
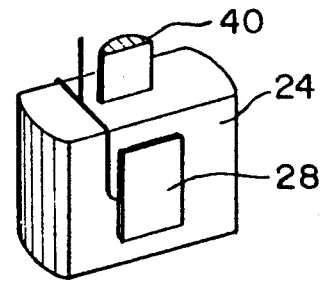
FIG. 1a is a perspective view of the FIG. 1 embodiment.
Figure 2:
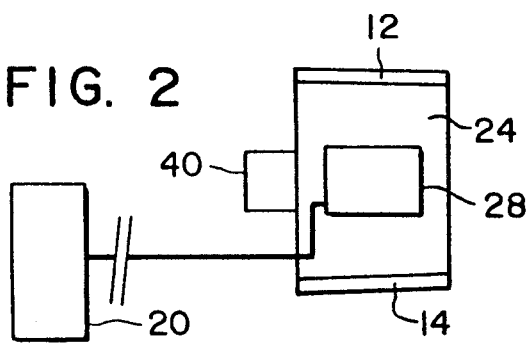
FIG. 2 is a side elevational view of the sensing plug of FIG. 1.

Referring to FIGS. 1 and 2, a sensing plug used in an apparatus and method for measuring rock-stress is generally referred to by the numeral 10. The sensing plug 10 has two opposing tapered sidewalls 12 and 14 which are oppositely curved. The sensing plug 10 is electrically coupled to a processor 20 located remotely from the sensing plug 10. The processor processes signals output from the sensing plug to determine rock-stress data. Any of the known processors or sensing means commercially available may be employed, including those described in U.S. Pat. No. 4,542,655.

The sensing plug 10 includes a pair of opposed flat sidewalls 22 and 24 which are machined in a plane parallel to the axis of the plug. The sensing elements, if strain gauges 26 and 28, or other similar means, are mounted to these flat surfaces. Alternatively, a vibrating wire-type sensor could be placed appropriately in the plug 10. Alternatively, the sensing plug 10 could be formed of a photoelastic material that itself displays stress or deformation changes that can be analyzed by conventionally known methods, or photoelectric gauges could placed on the ends/walls of the sensing plug.

Figure 3:
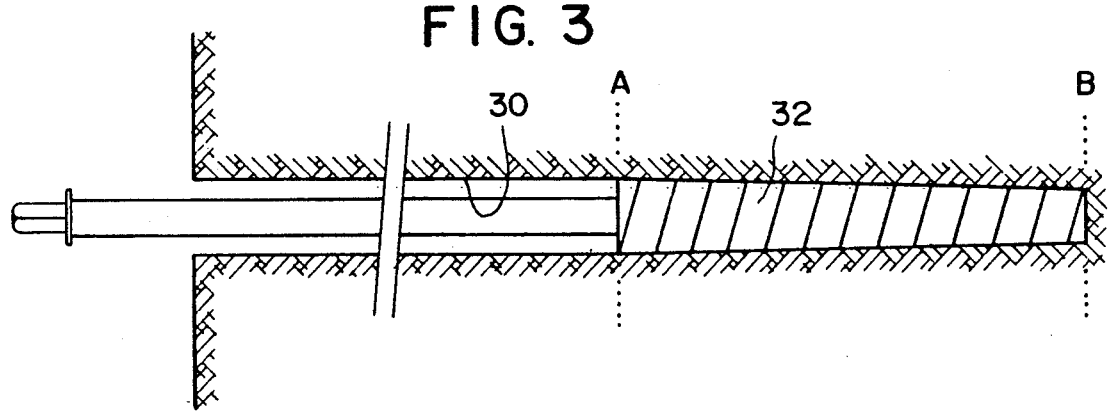
FIG. 3 is a schematic view of a borehole and tapered bit used in the method and apparatus of the present invention.
Figure 4:
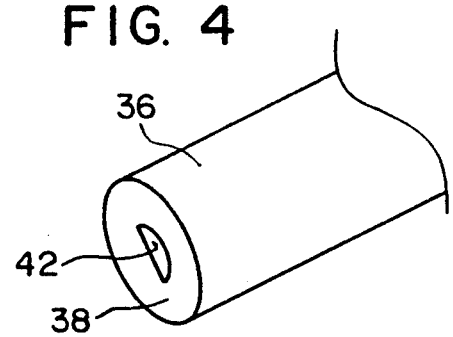
FIG. 4 is a perspective view of an end portion of a rod used in the method and apparatus of the present invention for inserting the sensing plug of FIG. 1.
Figure 5:
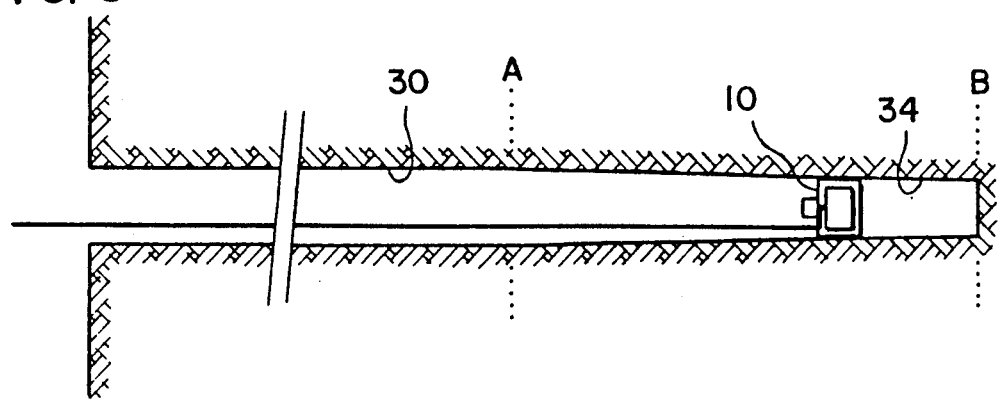
FIG. 5 is a schematic view showing a borehole with the sensing plug in place.

Referring to FIGS. 3-5, installation of the plug 10 is achieved by first drilling a cylindrical borehole 30 in earth material to be tested short of the desired depth of placement of the sensor. After first drilling the cylindrical borehole 30 with a conventional bit, a tapered drill bit 32 is used to drill beyond the first length, terminating approximately at the plane "A", to form a conically shaped inward end portion 34 of the cylindrical borehole 30. The tapered end portion extends from the plane A to about the plane "B". The drill bit 32 is preferably a conically shaped diamond encrusted bit or tool having similar hardness. The conicity of the drill bit 32 is preferably matched with that of the tapered sensing plug 10.

A rod 36 is used to insert the plug 10 into the conically shaped end portion 34 of the borehole 30 by detachably coupling the plug 10 to the end 38 of the rod 36. The detachable coupling is made by a protrusion 40 having a particular geometric shape, such as a "D", which is complementary and inter-fitting with a similarly geometrically shaped recess 42 formed in the end 38 of the rod 36.

The rod is inserted into the borehole 30 and moved fully into the borehole until the plug 10 is positioned in the conically shaped end portion 34 of the borehole 30. The proper orientation of the plug 10 is made by turning the rod. Once the proper orientation is achieved, the plug 10 is wedged in place and thereby prestressed by tapping or hammering the opposite end of the rod which protrudes outwardly from the borehole 30

Alternatively, the complementary connection between the plug 10 and the rod 36 may be a threaded connection so that once the plug is hammered into place, the rod could then be rotated to unscrew and thus disconnect the plug from the rod. After placing the plug firmly in the conically shaped portion 34, the sensor is then connected to appropriate commercially available data logging/recording/analysis devices, illustrated in FIG. 2 schematically as the processor 20.

An advantage of the present invention is that, if desired, two or more sensing plugs, each sized differently, can be placed in the same conical hole at different orientations in order to enable monitoring of stresses in each of the different directions. Also, this stress measuring device has the advantage that it could be easily removed from the hole by utilizing a rod with a hook-like means to grab the sensor plug around its end away from the hole opening, and tapping the rod to disengage the sensor from the hole.

Another advantage of the present invention is the ease and rapidity of placement possible with just a hammer and rod, which can be done by low-skilled labor at significant cost savings. This ease of installation is made possible by the drilling of a slightly conical hole for placement of the sensing or recording device, the conicity of the hole being the feature that enables placement without complicated installation tools or the need to bond or grout the sensing device in place. Also, the simplicity of the present structure and lack of any complicated structures, as commonly found in existing stress-meters, will enable low cost manufacture.

As is the case in the aforementioned U.S. Pat. No. 4,542,655, the sensing plug may be formed of metal, Plexiglas or other suitable composite material, depending on the desired stress response characteristics and method of analyzing the stresses. Also, the strain gauges and vibrating wire gauges described herein are generally known and commercially available. These gauges have leads which provide electrical output signals to a processor for calculating stress. A typical processor which may be used is a Strain Indicator model P-3500 or P-350A manufactured by Instruments Division, Measurement Group Incorporated of Raleigh, N.C. Observation of a photoelastic plug or photoelastic gauges is conventionally done by optical devices commercially available.

Numerous modifications and adaptations of the present invention will be apparent to those so skilled in the art and thus, it is intended by the following claims to cover all such modifications and adaptations which fall within the true spirit and scope of the invention.

I claim:

1. A method of measuring rock-stress comprising drilling a cylindrical borehole into earth material at a length short of a desired depth of placement;
   drilling beyond the first length with a tapered bit to form a conically shaped, inward end portion of the cylindrical borehole;
   inserting a tapered sensing plug into the conically shaped inward end portion of the cylindrical borehole;
   seating the sensing plug at a predetermined orientation firmly in the conically shaped inward end portion of the cylindrical borehole; and
   processing signals output by the sensing plug to determine rock-stress data.

2. A method according to claim 1, wherein the inserting comprises detachably coupling the sensing plug to an end of a rod and manipulating the rod axially to place the sensor plug in the conically shaped inward end portion of the cylindrical borehole.

3. A method according to claim 2, wherein the seating comprises turning the rod until the predetermined orientation is achieved, driving the rod further until the sensing plug is wedged firmly in the conically shaped inward end portion of the cylindrical borehole, detaching the rod from the sensing plug, and removing the rod.

4. A method according to claim 1, wherein the conicity of the tapered sensing plug, and conicity of the tapered drill bit from a conically shaped, inward end portion of the cylindrical borehole, matched for easy seating and removal of the plug in the borehole.

* * * * *